United States Patent [19]

Martin et al.

[11] Patent Number: 4,720,603
[45] Date of Patent: Jan. 19, 1988

[54] PREPARATION OF P-CYMENE AND HOMOLOGOUS ALKYLBENZENES

[75] Inventors: Roland Martin, Ludwingshafen; Walter Gramlich, Edingen-Neckarhausen, both of Fed. Rep. of Germany

[73] Assignee: BASF Aktiengesellschaft, Ludwigshafen, Fed. Rep. of Germany

[21] Appl. No.: 16,941

[22] Filed: Feb. 20, 1987

[30] Foreign Application Priority Data

Mar. 7, 1986 [DE] Fed. Rep. of Germany ....... 3607448

[51] Int. Cl.$^4$ .............................. C07C 5/32
[52] U.S. Cl. .................. 585/431; 585/432
[58] Field of Search .............. 585/431, 432

[56] References Cited

U.S. PATENT DOCUMENTS

| | | | |
|---|---|---|---|
| 2,272,711 | 2/1942 | Hull | 585/432 |
| 2,400,012 | 5/1946 | Littmann | 585/432 |
| 2,402,898 | 6/1946 | Kirkpatrick | 260/668 |
| 2,857,439 | 10/1958 | Glasebrook | 260/668 |
| 3,312,635 | 4/1967 | Liquori | 252/470 |
| 4,239,928 | 12/1980 | Takahashi et al. | 585/431 |

FOREIGN PATENT DOCUMENTS

| | | | |
|---|---|---|---|
| 570930 | 2/1959 | Canada | 585/432 |
| 0077289 | 8/1985 | European Pat. Off. | |

OTHER PUBLICATIONS

Bulletin of the Chemical Society of Japan, vol. 51 (12), 3641–3642 (1978).

Primary Examiner—Curtis R. Davis
Attorney, Agent, or Firm—Oblon, Fisher, Spivak, McClelland, & Maier

[57] ABSTRACT

Alkylbenzenes of the general formula I

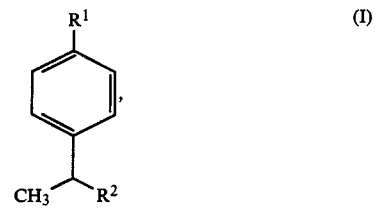

where $R^1$ is $C_1$–$C_4$-alkyl, preferably methyl, and $R^2$ is hydrogen or $C_1$–$C_4$-alkyl, preferably methyl, are prepared by catalytic aromatization of the corresponding alkenylcyclohexenes of the general formula II

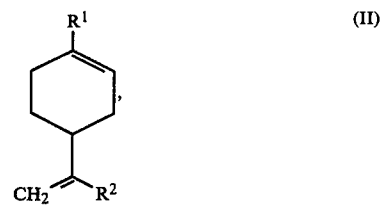

by carrying out the conversion in the gas phase at 150°–400° C. over a catalyst which contains palladium oxide and sulfur and/or selenium or selenium oxide on active carbon.

5 Claims, No Drawings

PREPARATION OF P-CYMENE AND HOMOLOGOUS ALKYLBENZENES

The present invention relates to a process for preparing alkylbenzene, in particular p-cymene, by catalytic conversion of alkenylcyclohexene.

U.S. Pat. No. 3,312,635 discloses the conversion of limonene over supported catalysts containing nickel oxide and molybdenum oxide at 200°–250° C. to mixtures of p-cymene, p-menthane and p-menthene.

Bull. Chem. Soc. Japan 51 (1978), 3641–42, discloses that the above conversion can also be carried out over magnesium oxide, calcium oxide or lanthanum oxide in the presence of hydrogen.

U.S. Pat. No. 2,857,439, furthermore, discloses that with numerous catalysts, in particular palladium, the product obtained on passing monocyclic terpenes in vapor form over the hot catalysts and subsequently condensing the vapors in mainly p-cymene. This patent specification says that these known processes are not advantageous if sulfur-contaminated terpenes are used. For that reason, this prior art proposes that sulfur-contaminated terpenes be passed in vapor form in the presence of hydrogen over particular hot supported platinum catalysts at 200°–500° C.

U.S. Pat. No. 2,402,898 discloses in addition that monocyclic terpenes can be aromatized to a p-cymene at about 300° C. over catalysts which contain noble metals such as Pd and Pt on active carbon. The disadvantage of this process is that the catalyst is sufficiently active only for a relatively short time.

More recently, European Pat. No. 77,289 disclosed a process for converting terpenes into cymenes by heating these terpenes in the presence of an alkali metal carbonate catalyst on an MgO carrier which has a surface area of not less than 20 m²/g. In the examples of this patent, this process is applied to turpentine oil, limonene and Δ-3-carene. The disadvantage with this process is that reaction temperatures of 400° C. or more are required, which on the one hand necessitates a very high energy consumption and on the other predicates a relatively rapid deactivation of the catalyst by decomposition products.

It is an object of the present invention to provide a catalyst which makes it possible to convert alkenylcyclohexenes of the general formula II into the corresponding alkylbenzenes in a particularly advantageous manner. The catalysts should be easily available, have a long life, be highly active and easily regenerated and should ensure a very high conversion with good selectivity at, ideally, a low reaction temperature.

We have found that this object is achieved with a process for preparing an alkylbenzene of the general formula I

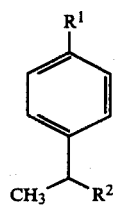

where $R^1$ is $C_1$–$C_4$-alkyl, preferably methyl, and $R^2$ is hydrogen or $C_1$–$C_4$-alkyl, preferably methyl, by catalytic aromatization of alkenylcyclohexene of the general formula II

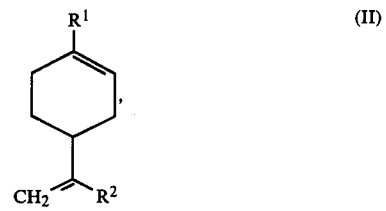

where $R^1$ and $R^2$ have the abovementioned meanings, which comprises carrying out the reaction in the gas phase at 150°–350° C. over a catalyst which contains palladium oxide and sulfur and/or selenium or selenium oxide on active carbon.

The process according to the invention substantially meets the requirements placed on the catalyst at the beginning. Surprisingly, the aromatization of the alkenylcyclohexene of the formula I on the catalyst according to the invention proceeds in a very high yield and with only very little in the way of byproduct formation. The dehydrogenation can be carried out in the absence of air or oxygen, thereby making a significant contribution to the safety of the process in the industry. Another surprise was the long catalyst life of up to several months compared, for example, with only 50 to 100 hours for the catalyst used in the process of U.S. Pat. No. 2,402,898.

This is particularly surprising since it is explained very plausibly in U.S. Pat. No. 2,857,439 that in the presence of sulfur in the terpenes used as starting material the known processes for aromatizing terpenes only give very unsatisfactory results since sulfur contaminates and thereby poisons the catalysts used, which leads to extremely short catalyst lives.

When the activity decreases, the catalyst according to the invention can be regenerated in a simple manner by atmospheric oxidation.

Catalysts used for the process according to the invention are active carbons which contain from 0.5 to 10% by weight, preferably from 1 to 7% by weight, of palladium oxide and from 0.1 to 2, preferably from 0.2 to 1, % by weight of sulfur and/or selenium or selenium dioxide.

In general, the catalysts are used in the form of extrudates of from 2 to 5 mm in length or tablets of from 1 to 4 mm in diameter.

The form of the catalysts depends on the reaction vessel. If the reaction is carried out in a fluidized bed reactor, a pulverulent fluidized catalyst of from 0.1 to 0.3 mm in particle size is used.

Preparation of the catalyst according to the invention comprises in general first spraying the active carbon, more strictly the active carbon pellets, in an impregnating drum in a conventional manner with a palladium nitrate solution, thoroughly drying the product at elevated temperatures and then, in a second impregnating step, spraying on an ammonium polysulfide solution or an aqueous solution of selenous acid and finally again thoroughly drying at elevated temperatures.

The conversion according to the invention is preferably carried out continuously under atmospheric pressure in a conventional manner, for example in a flow reactor or a fluidized bed reactor.

The aromatization is carried out at from 150° to 350° C., preferably from 200° to 300° C., by evaporating the alkenylcyclohexene and passing the vapor with oxygen as carrier gas over the hot catalyst. In the vapor mixture, the ratio of alkenylcyclohexene vapor: nitrogen ranges in general from 1:1 to 1:5, preferably from 1.5 to 2.5.

Workup is effected in a conventional manner, for example by distillation.

The alkenylcyclohexenes required as starting compounds are present in many plants or are obtained as byproducts in various industrial processes. For instance, limonene is present in citrus fruit and is obtained in large amounts as a byproduct in the production of fruit juices from oranges and/or lemons.

The alkenylcyclohexene used need not necessarily be 100% pure, but a purity of more than 90% is advisable if the resulting alkylbenzene is to be usable without further purification. This applys in particular to the aromatization of limonene, since the p-cymene resulting therefrom itself finds utility as a scent and is also used as an intermediate for further desired scents such as cuminaldehyde and cyclamenaldehyde, for which a high purity of the p-cymene is a prerequisite.

The Examples below illustrate the subject-matter of the invention.

EXAMPLES 1 TO 3

Comparative Examples 1 and 2

In each case, the amount of d-limonene (purity: 96 GC area %) evident from the table below was vaporized and passed diluted with nitrogen in a ratio of about 1:2 over the catalyst in a tubular reactor (600 mm in length and 30 mm in diameter), the catalyst having been heated to the temperature evident in the table, having the composition evident in the table and being present in the form of 4 mm extrudates. The starting materials and reaction products were determined by gas chromatography and by a $^1$H-NMR and IR spectroscopy. The conversion was 100% in all cases.

trudates). Even after conversion of 1490 kg of limonene over the same catalyst in the course of about 3 months, the catalyst was still as active as at the start of the long-term test; the conversion was always 100%; the yield was from 96 to 97% of theory.

We claim:

1. A process for preparing an alkylbenzene of the general formula I

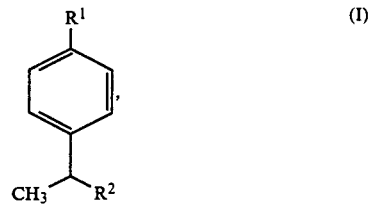

where $R^1$ is $C_1$-$C_4$-alkyl and $R^2$ is hydrogen or $C_1$-$C_4$-alkyl, by catalytic aromatization of an alkenylcyclohexene of the general formula II

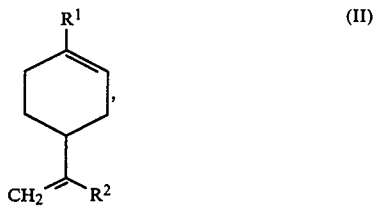

where $R^1$ and $R^2$ have the abovementioned meanings, which comprises carrying out the reaction in the gas phase at 150°–350° C. over a catalyst which contains palladium oxide and sulfur and/or selenium or selenium oxide on active carbon.

2. A process as claimed in claim 1, wherein the conversion is carried out in the absence of air or oxygen.

3. A process as claimed in claim 1, wherein the conversion is carried out at 200°–300° C.

TABLE

| | Catalyst | | | | | p-cymene obtained | |
|---|---|---|---|---|---|---|---|
| | Composition | Amount [g] | Temperature [°C.] | d-limonene [kg] | [kg] | Purity [GC area %] | Yield [% of theory] |
| Example | | | | | | | |
| 1 | 5.75% of PdO + 0.25% of S on active carbon | 90 | 220–230 | 62 | 59.5 | 96 | 97 |
| 2 | 5.75% of PdO + 1% of S on active carbon | 86 | 250 | 31.5 | 31 | 95 | 98 |
| 3 | 5.75% of PdO + Se (calc. 0.35% of SeO$_2$) on active carbon | 98 | 260 | 9.06* | 8.6 | 95 | 92 |
| Comparative Example | | | | | | | |
| 1 | 0.5% of Pd on Al$_2$O$_3$ | 100 | 230 | 1.89 | 1.8 | 70 | 69 |
| 2 | 5% of Pd on active carbon | 118 | 230 | 5.03 | 4.7 | 89 | 88 |

*Purity 99%

EXAMPLE 4

About 1 l/h (5.8 mol/h) of α-limonene (purity: 99 GC area %) was vaporized to give about 130 l/h of limonene vapor. This limonene vapor was passed, diluted with about 200 to 250 l of N$_2$/h, inside a tubular reactor (2 m in length; 4 cm in diameter; 3 l capacity), over a hot catalyst at 230°–250° C. composed of 5.75% of PdO+0.25% of S on active carbon pellets (4-mm ex- 4. A process as claimed in claim 1, wherein the conversion is carried out over a catalyst which contains palladium oxide in an amount of from 0.5 to 10% by weight as well as from 0.1 to 2% by weight of sulfur and/or selenium or selenium oxide.

5. A process as claimed in claim 1, wherein, to prepare p-cymene, limonene is vaporized and passed with nitrogen as carrier gas over the hot catalyst.

* * * * *